US011951271B2

(12) United States Patent
Ma et al.

(10) Patent No.: US 11,951,271 B2
(45) Date of Patent: Apr. 9, 2024

(54) METHOD OF MANUFACTURING AN IN-PLANE METAL MICRONEEDLE ARRAY

(71) Applicant: DALIAN UNIVERSITY OF TECHNOLOGY, Liaoning (CN)

(72) Inventors: Guojun Ma, Liaoning (CN); Chengwei Wu, Liaoning (CN); Xiaolong An, Liaoning (CN); Xiao Han, Liaoning (CN); Wei Zhang, Liaoning (CN); Yongtao Lv, Liaoning (CN); Jianli Ma, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 947 days.

(21) Appl. No.: 16/960,177

(22) PCT Filed: May 13, 2019

(86) PCT No.: PCT/CN2019/086697
§ 371 (c)(1),
(2) Date: Jul. 6, 2020

(87) PCT Pub. No.: WO2020/227900
PCT Pub. Date: Nov. 19, 2020

(65) Prior Publication Data
US 2021/0046298 A1 Feb. 18, 2021

(51) Int. Cl.
A61M 37/00 (2006.01)
B23P 17/04 (2006.01)

(52) U.S. Cl.
CPC ......... A61M 37/0015 (2013.01); B23P 17/04 (2013.01); A61M 2037/0053 (2013.01); Y10T 29/49995 (2015.01)

(58) Field of Classification Search
CPC ........... B23P 17/04; A61M 2037/0053; Y10T 29/49995
See application file for complete search history.

(56) References Cited

U.S. PATENT DOCUMENTS 7,048,723 B1 * 5/2006 Frazier ............. A61M 37/0015
604/274
7,497,980 B2 * 3/2009 Xu .................... A61M 37/0015
264/219

(Continued)

FOREIGN PATENT DOCUMENTS

CN  106512199 A   3/2017
KR  10-0682534 B1  2/2007

Primary Examiner — Sarang Afzali
(74) Attorney, Agent, or Firm — Muncy, Geissler, Olds & Lowe, P.C.

(57) ABSTRACT

A high aspect ratio in-plane metal microneedle array, a manufacturing method and a clamping and inserting auxiliary device thereof is disclosed. A large-size metal sheet is cut into small metal sheets. A clamping tooling composed of two upper and lower metal cover plates is processed. Inner sides of the upper and the lower cover plates of the tooling are provided with grooves in which the metal sheets are placed and fastened by bolts. Wire cutting is conducted on the tooling and the metal sheets as a whole to obtain a plane metal microneedle array with a plurality of microneedle bodies. In addition, an assembling and clamping device and an inserting auxiliary device of the high aspect ratio in-plane metal microneedle array is provided. The assembled inserting auxiliary device is placed on skin, and the microneedle array is inserted into the skin through the auxiliary device.

2 Claims, 6 Drawing Sheets

(56) References Cited

U.S. PATENT DOCUMENTS

| | | | |
|---|---|---|---|
| 11,738,185 B2 * | 8/2023 | Ma | B21G 1/003 |
| | | | 604/173 |
| 2011/0021996 A1 * | 1/2011 | Lee | A61M 37/0015 |
| | | | 604/173 |

* cited by examiner

METHOD OF MANUFACTURING AN IN-PLANE METAL MICRONEEDLE ARRAY

TECHNICAL FIELD

The present invention belongs to the technical field of medical apparatuses, and relates to a method of manufacturing an in-plane metal microneedle array.

BACKGROUND

A microneedle (MN) generally refers to a miniature needle with a length of tens of microns to a few millimeters and a tip diameter of tens of microns or less. A microneedle is used to pierce stratum corneum of skin to break through the biological barrier effect of the stratum corneum of the skin and form a micron-level drug delivery channel. Experiments show that the transdermal drug delivery efficiency can be increased by orders of magnitude, and simultaneously, the types and ranges of transdermal drug delivery are also been greatly expanded. In addition, due to the small size of the microneedle, the invasiveness and pain caused by piercing the skin are very small, which does not cause obvious discomfort for patients subjected to drug delivery, and is conducive to preventing infections and more conducive to wound recovery. Because of the above advantages, in recent ten years, the microneedle technology has been widely concerned in the field of transdermal drug delivery.

Besides transdermal drug delivery, in recent years, the microneedle has received more and more attention in the field of biomedical measurement and micro sampling analysis. However, unlike the transdermal drug delivery technology in which the microneedle only needs to pierce the skin surface tissue, the microneedle used for the biological micro sampling analysis needs to insert into the tissue by a certain depth. Thus, the length of the sampling microneedle is often in the magnitude of millimeters. To make the sampling microneedle still have the advantages of less invasiveness and less pain, the lateral dimension of the sampling microneedle still needs to be as small as possible, so that the aspect ratio of the sampling microneedle is very large, thereby bringing difficulties to the manufacture and use of the sampling microneedle. Firstly, the higher the height of the microneedle is, the higher the processing difficulty and cost are. The existing conventional microneedle processing technologies such as photolithography, deep reactive ion etching and X-ray lithography are difficult to process a high aspect microneedle. Secondly, the long and thin size of the high aspect microneedle is easy to induce buckling or breakage of the microneedle in the process of inserting into the skin, leading to a failure to insert.

With respect to the manufacturing problem of high aspect sampling microneedle, Korean scholars have successfully manufactured a sampling microneedle with a length of 2 mm through polymer drawing molding with combination of metal plating technology, which is called "ultra-high aspect microneedle". Related achievements were also published in the authoritative magazine <Advanced Materials>. Simply speaking, the technology uses a drawing head with a plurality of micron-level microcolumns to draw SU-8 glue in a molten state. The SU-8 glue is drawn into a column with controllable height. After cooling and shaping, the surface of the columnar SU-8 glue is coated with metal, and then the SU-8 glue is dissolved but a metal coating is reserved. Finally, a high aspect metal sampling microneedle array with height of millimeter level is obtained. Obviously, the manufacturing technology is ingeniously designed and can successfully manufacture high aspect ratio metal microneedles. However, the manufacturing technology is relatively complicated, high in cost and difficult to realize batch production. In addition, how to ensure that the microneedle array formed by high aspect ratio columnar microneedles does not buckle or break when inserting into the skin is still not effectively solved.

SUMMARY

In view of the problems in the process of manufacturing and using a high aspect ratio sampling microneedle, the present invention provides a high aspect ratio in-plane metal microneedle array, a preparation method and a clamping and inserting auxiliary device thereof. The present invention has the advantages of high efficiency, low cost and good performance and is suitable for batch production and actual use.

To achieve the above object, the present invention provides the following technical solution:

A Preparation Method for a High Aspect Ratio In-Plane Metal Microneedle Array Comprises the Following Steps:

Step 1: using medical stainless steel or titanium alloy metal sheet material with good biocompatibility and excellent strength and toughness as a microneedle material, wherein the thickness of a metal sheet is 20-200 microns.

Step 2: cutting the metal sheet into small metal sheets 5 with proper sizes, wherein recommended sizes are: 30-50 mm in length and 10-30 mm in width.

Step 3: processing a special sheet clamping tooling.

The tooling is composed of two identical upper and lower metal cover plates 1, and the overall thickness of each cover plate is 5-10 mm; inner walls of the upper and the lower cover plates of the tooling are processed with grooves 2 matched with the sizes of the small metal sheets 5, i.e., the lengths and widths of the grooves are consistent with the lengths and widths of the metal sheets 5 to place the metal sheets 5; the depths of the grooves of the upper and the lower cover plates are 1-5 mm; through holes 3 for passing through fastening bolts 4 are processed at edges around upper and the lower cover plate bodies 1. The clamping tooling is made of metal material such as stainless steel and 45 #steel with good electrical conductivity and high strength.

Step 4: placing the small metal sheets 5 in the groove 2 of any metal cover plate 1; adjusting the number of the metal sheets 5 placed at one time according to the thickness of the sheets and the depth of the groove; recommending placing 20-200 metal sheets at one time; placing another metal cover plate 1 on the cover plate on which the metal sheets 5 are placed, with the groove facing the metal sheets 5 and aligned up and down; then encapsulating and fastening the upper and the lower metal cover plates 1 by the fastening bolts 4, and compacting the metal sheets 5 to form a whole with the upper and the lower cover plates 1.

Step 5: designing the geometries and sizes of sheet plane metal microneedles.

A sheet plane metal microneedle array is composed of substrates 6 and high aspect ratio microneedle bodies 7 for a subsequent clamping part; the height of the high aspect ratio microneedle bodies 7 is 1-5 mm, the width of a root of each microneedle body is 50-500 microns, and the thickness is the thickness of the metal sheet 5. The high aspect ratio microneedle bodies 7 are arranged above the substrates 6; the number of the microneedles on each substrate is 3-50, and a distance is 0.25-10 mm. Positioning shoulders 8 are arranged on both sides above the substrates 6 for positioning guidance of an inserting auxiliary device; and a positioning guide groove 9 is arranged in the lower middle of each substrate 6 for subsequent assembly of each substrate 6.

The high aspect ratio microneedle bodies 7 adopt equal-strength design along a length direction, that is, the width change of the high aspect ratio microneedle bodies 7 needs to ensure that the microneedle bodies 7 have the same maximum bending stress at each cross section when tips are subjected to a transverse concentrated load. If the root of each microneedle body 7 is a starting point of x axis, the x axis is located on a longitudinal symmetry axis of each microneedle body 7, and a width direction is assumed to be a y axis, then the equal-strength design requires that x and y satisfy the following relationship: $y=C\sqrt{L_0-x}$; in the formula, $L_0$ is the length of the microneedle bodies 7, and C is a constant which comprehensively reflects the yield strength of the material, the thickness of the microneedles, and a load size.

Step 6: clamping the metal sheets and the tooling encapsulated in step 4 to a wire cutting device, determining a wire path according to the geometry and sizes of the sheet plane metal microneedles designed in step 5 by the wire cutting device, conducting wire cutting on the tooling and the metal sheets 5 as a whole, and processing the metal sheets 5 into the substrates 6 and the microneedle bodies 7. In the wire cutting process, the tips of the microneedle bodies 7 are cut with an "8"-shaped path to ensure the sharpness of microneedle tips. In addition, during processing, both sides of the substrates 6 are not completely cut, and are reserved for 2 to 5 mm of uncut part 10 to keep the integrity of the clamping tooling, to ensure that the clamping tooling and the metal sheets 5 still form a whole after processing, thereby not only preventing the metal microneedle array from being washed away by cooling liquid during processing, but also ensuring that the used tooling still has sufficiently high structural rigidity so that the tooling can be reused.

Step 7: taking off the fastening bolts 4 on the tooling, and taking out and washing the processed metal sheets 5 to obtain microneedle substrates which are not cut.

Step 8: cutting the microneedle substrates obtained in step 7, and removing the material on regions reserved on both sides of the substrates 6 to separate the sheet plane metal microneedles from the metal sheets 5 to obtain a sheet plane metal microneedle array with a plurality of microneedle bodies.

A high aspect ratio in-plane metal microneedle array is disclosed. The sheet in-plane metal microneedle array is composed of substrates 6 and high aspect ratio microneedle bodies 7 for a subsequent clamping part; the height of the high aspect ratio microneedle bodies 7 is 1-5 mm, the width of a root of each microneedle body is 50-500 microns, and the thickness is the thickness of the metal sheet 5. The high aspect ratio microneedle bodies 7 are arranged above the substrates 6; the number of the microneedles on each substrate is 3-50, and a distance is 0.25-10 mm. Positioning shoulders 8 are arranged on both sides above the substrates 6 for positioning guidance of an inserting auxiliary device; and a positioning guide groove 9 is arranged in the lower middle of each substrate 6 for subsequent assembly of each substrate 6. The high aspect ratio microneedle bodies 7 adopt equal-strength design along a length direction, that is, the width change of the high aspect ratio microneedle bodies 7 needs to ensure that the microneedle bodies 7 have the same maximum bending stress at each cross section when tips are subjected to a transverse concentrated load. If the root of each microneedle body 7 is a starting point of x axis, the x axis is located on a longitudinal symmetry axis of each microneedle body 7, and a width direction is assumed to be a y axis, then the equal-strength design requires that x and y satisfy the following relationship: $y=C\sqrt{L_0-x}$; in the formula, $L_0$ is the length of the microneedle bodies 7, and C is a constant which comprehensively reflects the yield strength of the material, the thickness of the microneedles, and a load size.

An assembling and clamping device of a high aspect ratio in-plane metal microneedle array is disclosed. A special microneedle sheet assembling and clamping device comprises a main body 11 and a partition board 15; the main body 11 and the partition board 15 are made of light metal or polymer material, and aluminum alloy or polytetrafluoroethylene and the like are selected, but not limited to the two materials.

The main body 11 is a box-shaped rectangular structure with one side open, and the bottom of an inner cavity is provided with a slide rail 12 matched with the guide groove 9 at the bottom of each microneedle substrate. The bottom of the main body 11 is provided with a threaded hole 13 for subsequent installation of a handle. A threaded through hole 14 is arranged on the side surface of the main body 11 for pressing the partition board 15 by a bolt 16. The high aspect ratio in-plane metal microneedle array is vertically placed in the assembling and clamping device, with the microneedle bodies 7 facing upward. The width of a cavity of the main body 11 is consistent with the width of the microneedle substrates 6. The depth of the cavity is consistent with the height of the outer edge of each substrate 6 (excluding the height of the microneedle bodies 7 and the positioning shoulders), that is, the plane of the positioning shoulders of the substrates 6 is the same as the plane of the upper surface of the main body 11. The length of the cavity is determined according to the number of the microneedle substrates to be clamped and the distances between the substrates, and a recommended length range is 10-40 mm. The partition board 15 is of a thin rectangular structure, and is used for positioning each microneedle substrate when the microneedle array is assembled. The width of the partition board 15 is consistent with the depth of the cavity of the main body 11, the length is consistent with the width of the cavity of the main body 11 and the thickness is 1-5 mm. The bottom of the partition board 15 is provided with a groove matched with the guide groove 9 at the bottom of each substrate 6.

The high aspect ratio in-plane metal microneedle array is vertically placed in the cavity of the main body 11 of the clamping device, and each substrate is separated by the partition board 15. The bolt 16 penetrates through the threaded through hole 14 on the side surface of the clamping device and extrudes the partition board 15 to keep each microneedle substrate stable. During clamping, the side of each microneedle substrate close to each microneedle body is higher than the upper surfaces of the partition board 15 and the main body of the clamping device. The specific exceeding value is determined by the sizes of the positioning shoulders 8 on both sides of the microneedle substrates 6. After clamping, a hand-held handle 17 is installed at the threaded hole 13 at the bottom of the main body 11 of the clamping device to complete the assembly and clamping of the high aspect ratio in-plane metal microneedle array.

An inserting auxiliary device of a high aspect ratio in-plane metal microneedle array is disclosed. The inserting auxiliary device comprises a rectangular frame main body 18, a positioning partition board 20, and positioning small spacers 21; the rectangular frame main body 18 and the positioning partition board 20 are made of light metal or polymer material, and aluminum alloy or polytetrafluoroethylene and the like are selected, but not limited to the two materials. The positioning small spacers 21 and the microneedle substrates 6 are made of the same material.

The rectangular frame main body 18 is a frame-shaped cuboid which is open up and down, and is placed above the assembling and clamping device. The length and the width of an inner frame of the rectangular frame main body 18 are consistent with the length and the width of the cavity of the main body 11 of the clamping device. The height of the rectangular frame main body 18 is consistent with the height of the positioning shoulders 8 on both sides of the microneedle substrates. Both sides of the rectangular frame main body 18 are provided with threaded through holes 19 through which capless bolts 22 pass, for subsequent tightening. The positioning partition board 20 is specifically shown in FIG. 20. The height of the positioning partition board 20 is consistent with the height of the rectangular frame main body 18, and the length of the positioning partition board 20 is consistent with the length of the partition board 15 of the clamping device. The thickness of the positioning partition board 20 is consistent with the thickness of the partition board 15 of the clamping device, and the corresponding positions of the positioning partition board 20 and the microneedle bodies are lightly sanded with fine sandpaper. Every two positioning partition boards 20 are separated by the positioning small spacer 21, and a gap 23 between the two positioning partition boards 20 is used for the microneedle bodies 7 to pass. The height of the positioning small spacers 21 is consistent with the height of the positioning partition board 20, the width is smaller than the width of the positioning shoulders 8 on both sides of the microneedle substrate (6) by 0.1-1 mm, and the thickness is consistent with that of the microneedle substrates to ensure that the gap 23 between the positioning partition boards 20 is consistent with the thickness of the microneedle substrates.

The positioning partition board 20 is assembled into the rectangular frame main body 18; the positioning small spacers 21 are placed at both ends of each positioning partition board 20 to make the distance of the positioning partition boards 20 consistent with the thickness of the microneedles; and the contact position between the positioning partition boards 20 and the microneedle bodies is sanded to ensure that gaps exist between the microneedle bodies and the positioning partition boards 20 to avoid serious scratching. The capless bolts 22 pass through the threaded hole on one side of the end surface of the rectangular frame main body 18 to press the positioning partition boards 20 and the positioning small spacers 21 and maintain a one-to-one correspondence with the clamping device. A skin region to be inserted is sterilized; the assembled inserting auxiliary device is placed on the skin; and the assembled microneedle array is inserted into the skin through the gap 23 of the positioning partition boards 20 in the auxiliary device.

Further, considering the reliability of use, 502 glue is used at both ends of the positioning partition boards 20 to reinforce the connection among the partition boards 20, the positioning small spacers 21 and the rectangular frame main body 18.

Compared with the Prior Art, the Present Invention has the Beneficial Effects that:

(1) The design of the sheet in-plane microneedles is conducive to simplifying the processing procedure, and the sheet plane microneedles are flexible to use, and can be simply assembled into three-dimensional microneedle arrays of different specifications. The metal microneedle arrays can be processed in batches at one time. The present invention greatly improves the efficiency compared with other microneedle processing methods. Moreover, the wire cutting processing technology has relatively low cost. Thus, the microneedle array processing method provided by the present invention has low cost.

(2) After the clamping tool is used, except that the material at the path of a cutting wire is cut off, other parts are still intact. In one aspect, it can ensure that the tooling has sufficiently high rigidity for subsequent repeated clamping; and in another aspect, because the tooling material at the processing path has been cut off, only the metal sheet needs to be cut in subsequent use, thereby further increasing the number of the metal microneedles that can be processed at one time, improving the efficiency and reducing the cost. If a single metal sheet is cut, the microneedles may be deformed by a small lateral force due to small thickness. When the height of the microneedles to be processed is large, the deformation is great and the accuracy is more difficult to guarantee. The clamping tooling compacts a plurality of metal sheets into a whole, which can enhance the stiffness of the workpiece, prevent processing size deviations caused by the lateral force during cutting, significantly improve the accuracy and length of the microneedles that can be processed and satisfy the processing needs of the high aspect ratio microneedles.

(3) During processing, the microneedle tips are cut with an "8"-shaped processing path, which can effectively avoid tip passivation caused by direct direction change of the tips, thereby ensuring the processing accuracy of the microneedle tips. The microneedles adopt the equal-strength design along the width direction, which can effectively improve the anti-buckling capability of the microneedles along the width direction, and prevent the microneedles from buckling and failing along the width direction when the microneedles are inserted into the skin. Meanwhile, a special inserting auxiliary device is used to provide additional constraints for the microneedles in the thickness direction, which can effectively improve the anti-buckling capability of the microneedles along the thickness direction and prevent the microneedles from buckling and failing along the thickness direction when the microneedles are inserted into the skin, thereby comprehensively improving the use reliability of the high aspect ratio microneedles.

Figure 1:
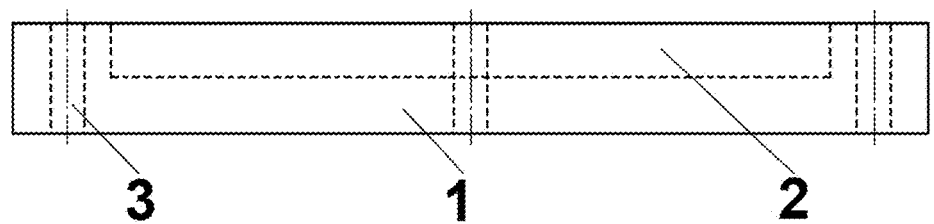
FIG. 1 is a front view in three views of a clamping device for processing.

In the figures: 1 upper and lower cover plate bodies; 2 groove; 3 bolt through hole; 4 fastening bolt; 5 metal foil; 6 substrate; 7 microneedle body; 8 positioning shoulder; 9 guide groove; 10 uncut part to keep the integrity of clamping tooling; 11 main body of assembling and clamping device; 12 slide rail; 13 threaded hole; 14 threaded through hole; 15 partition board; 16 bolt; 17 hand-held handle; 18 rectangular frame main body; 19 threaded through hole; 20 positioning partition board; 21 positioning small spacer; 22 capless bolt; and 23 gap.

DETAILED DESCRIPTION

The technical solution of the present invention is described below in detail with reference to drawings. The metal microneedle arrays can be processed in batches at one time in the present invention. Through calculation based on the ideal total cutting thickness of 2 cm for wire cutting, for example, the up-down overall wall thickness of the tooling is 5 mm, the depth of the grooves is 2 mm and the thickness of each metal sheet is 100 microns. Then, the number of the microneedles that can be cut at one time is 140, which greatly improves the efficiency compared with other microneedle processing methods. Moreover, the wire cutting processing technology has relatively low cost. Thus, the microneedle array processing method provided by the present invention has low cost. After the clamping tool is used, except that the material at the path of a cutting wire is cut off, other parts are still intact, thereby improving the efficiency and reducing the cost. The clamping tooling compacts a plurality of metal sheets into a whole, which can enhance the stiffness of the workpiece, prevent processing size deviations caused by the lateral force during cutting, significantly improve the accuracy and length of the microneedles that can be processed and satisfy the processing needs of the high aspect ratio microneedles. The microneedle tips are cut with an "8"-shaped processing path, thereby ensuring the processing accuracy of the microneedle tips. The microneedles adopt the equal-strength design along the width direction, which can improve the anti-buckling capability of the microneedles along the width direction, and prevent the microneedles from buckling and failing along the width direction when the microneedles are inserted into the skin. Meanwhile, a special inserting auxiliary device is used to provide additional constraints for the microneedles in the thickness direction, thereby comprehensively improving the use reliability of the high aspect ratio microneedles. Specific embodiments are as follows:

A Preparation Method for a High Aspect Ratio In-Plane Metal Microneedle Array Comprises the Following Steps:

Step 1: using metal sheet material with good biocompatibility and excellent strength and toughness as the microneedle material. Medical 304 stainless steel sheets are adopted in the present embodiment. The stainless steel sheets have the sizes of 1000 mm in length, 100 mm in width and 80 microns in thickness.

Step 2: cutting the metal sheets in step 1 into small metal sheets 5 with proper sizes, wherein in the present embodiment, length is 50 mm, width is 25 mm and thickness is 80 microns.

Figure 2:
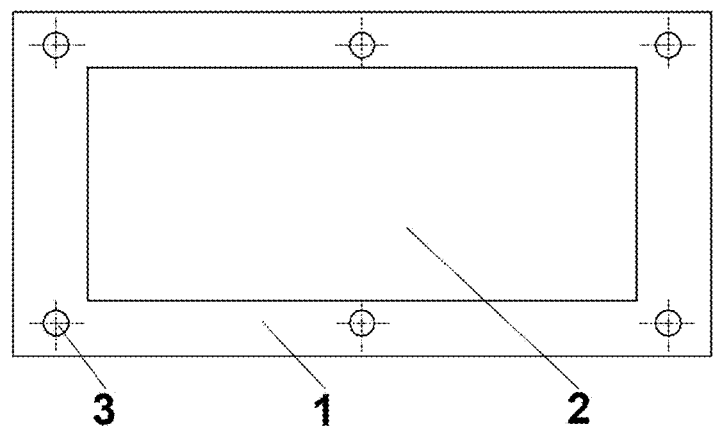
FIG. 2 is a top view in three views of a clamping device for processing.
Figure 3:
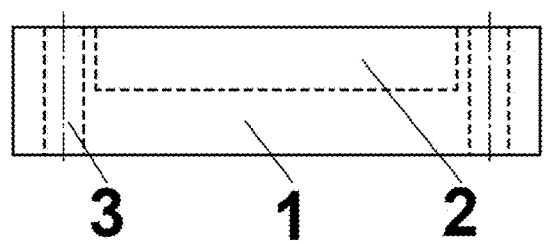
FIG. 3 is a side view in three views of a clamping device for processing.

Step 3: processing a special sheet clamping tooling, wherein the outer structure of the tooling is shown in FIG. 1, FIG. 2 and FIG. 3.

The clamping tooling is composed of two identical upper and lower metal cover plates 1. In the present embodiment, the upper and lower cover plates of the clamping tooling have length of 80 mm, width of 55 mm and thickness of 6 mm. Inner walls of the cover plates are provided with grooves 2 matched with the sizes of the small sheets of S2. In the present embodiment, the grooves have depths of 1.5 mm, lengths of 50 mm and widths of 25 mm. In the present embodiment, the tooling is made of stainless steel with good electrical conductivity and high strength. Six M6 bolt through holes 3 for subsequent bolt connection and fixation are processed on both sides of the clamping tooling, and the number of the holes can be adjusted according to actual needs.

Figure 4:
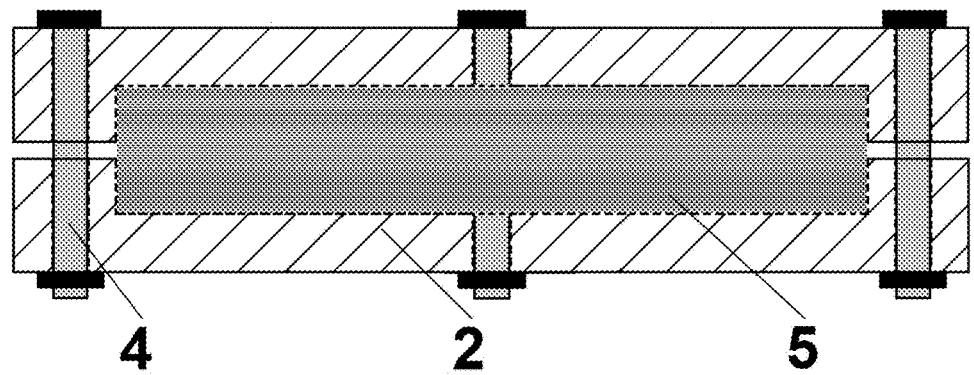
FIG. 4 is a schematic diagram after a metal substrate is clamped and installed.

Step 4: placing 100 small metal sheets 5 in the groove 2 of any metal cover plate 1 for stacking; recommending placing 20-200 metal sheets at one time; placing another metal cover plate 1 on the cover plate on which the metal sheets 5 are placed, with the groove facing the metal sheets 5 and aligned up and down; then encapsulating and fastening the upper and the lower metal cover plates 1 by the fastening bolts 4, and compacting the metal sheets 5 to form a whole with the upper and the lower cover plates 1 to obtain the whole of the encapsulated metal sheets and the processed clamping tooling as shown in FIG. 4.

Step 5: designing the geometries and sizes of sheet in-plane metal microneedles.

Figure 5:
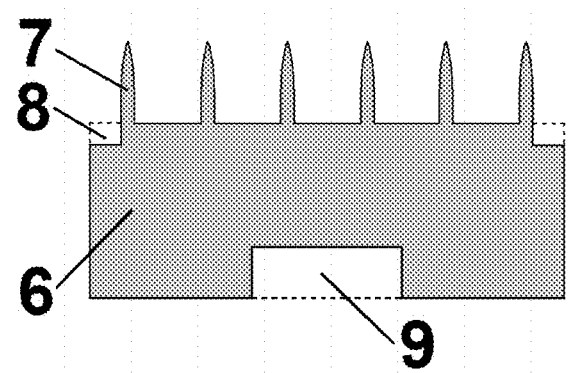
FIG. 5 is a schematic diagram of a sheet in-plane microneedle array with equal-strength microneedle bodies.

A sheet in-plane metal microneedle array is composed of substrates 6 and high aspect ratio microneedle bodies 7 for a subsequent clamping part. In the present embodiment, the shape of the microneedle bodies in the sheet microneedle array is shown in FIG. 5. The thickness of the microneedle bodies 7 is the thickness of the metal sheets. The microneedle bodies adopt equal-strength design along the width direction, that is, the width change of the microneedles needs to ensure that the microneedles have the same maximum bending stress at each cross section when tips are subjected to a transverse concentrated load. If the root of each microneedle is a starting point of x axis, the x axis is a longitudinal symmetry axis of each microneedle, and the width direction is assumed to be a y axis, then the equal-strength design requires that x and y satisfy the following relationship: $y = C\sqrt{L_0 - x}$; in the formula, $L_0$ is the length of the microneedles, and C is a constant. In the present embodiment, the microneedle bodies have height of 1.5 mm and bottom width of 150 microns; and C can be calculated as 0.0612 according to the bottom width and length of the microneedles. FIG. 5 is a schematic diagram of a single microneedle array. 8 in FIG. 5 is a positioning shoulder which is reserved for subsequently inserting and positioning the auxiliary device; and 9 in FIG. 5 is a positioning groove for subsequently assembling the substrates.

In the present embodiment, if the number of the microneedles on a single substrate is selected as 7, the distance is 3.5 mm, the height of each substrate excluding the microneedle body is 13 mm, and the bottom is provided with a groove 9 as shown in FIG. 5. In the present embodiment, the groove has height of 5 mm and width of 5 mm. Positioning shoulders 8 as shown in FIG. 5 are reserved on both sides of the microneedle substrate near the microneedle body for subsequent positioning when the microneedle array is inserted. In the present embodiment, the sizes of the part are 3 mm in height and 3 mm in width.

Figure 6:
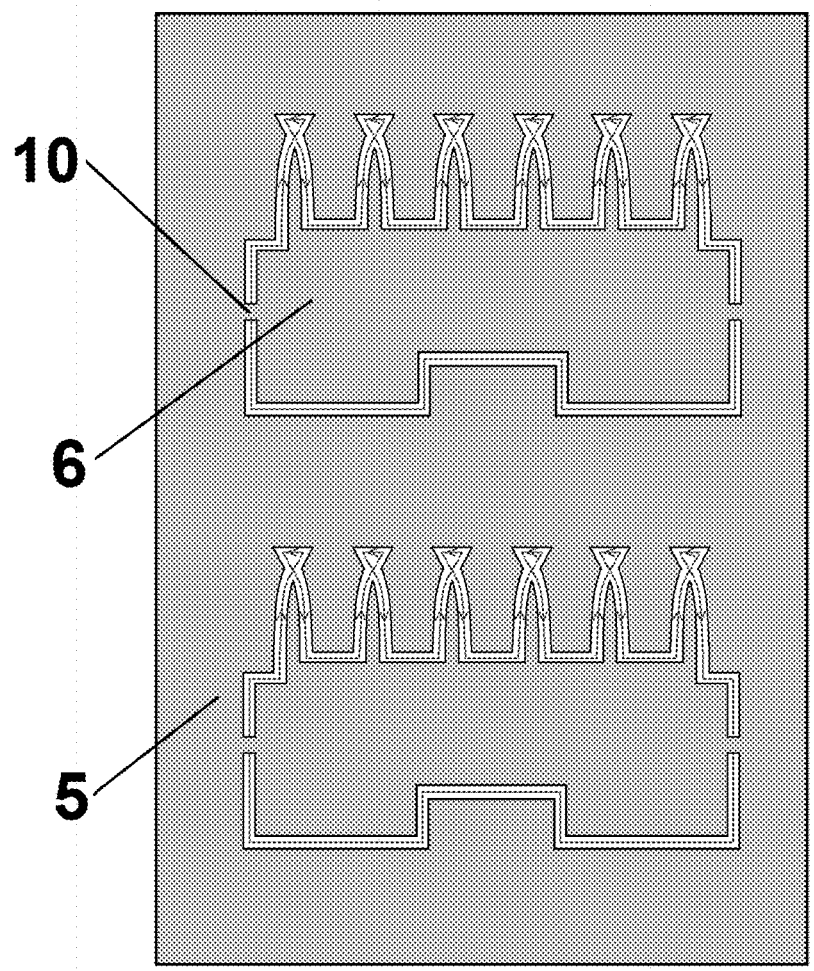
FIG. 6 is a schematic diagram of a wire cutting processing path.
Figure 7:
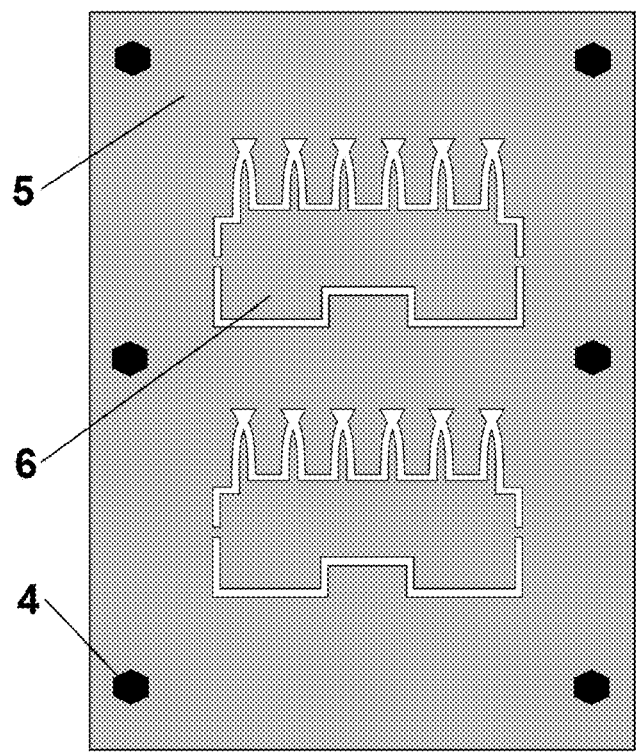
FIG. 7 is a schematic diagram of a clamping tooling and a microneedle array substrate which are not disassembled after cutting is completed.

Step 6: clamping the metal sheets and the tooling encapsulated in step 4 to a wire cutting device, determining a wire path according to the geometry and sizes of the sheet in-plane metal microneedles designed in step 5 by the wire cutting device, conducting wire cutting on the tooling and the metal sheets 5 as a whole according to the wire path shown in FIG. 6, and processing the metal sheets 5 into the substrates 6 and the microneedle bodies 7. In the wire cutting process, the tips of the microneedle bodies 7 are cut with an "8"-shaped path to ensure the sharpness of microneedle tips. In addition, during processing, a small amount of material is reserved on both sides of a single microneedle substrate as shown by the reference number "10" in FIG. 6 or FIG. 7 and is not cut. In the present embodiment, the height of the uncut part is 2 mm and the width is 2 mm. A schematic diagram (top view) when the metal sheets and the tooling after cut are not disassembled is shown in FIG. 7.

Figure 8:
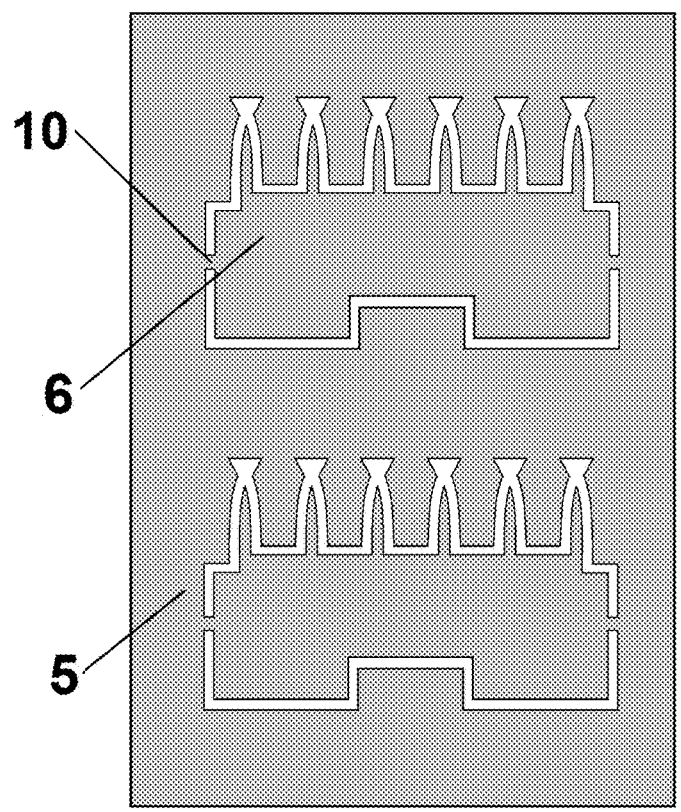
FIG. 8 is an overall schematic diagram of a sheet microneedle array and a substrate after cutting is completed.

Step 7: taking off the fastening bolts 4 on the tooling, and taking out and washing the processed metal sheets 5 to obtain microneedle substrates which are not cut as shown in FIG. 8.

Step 8: cutting the microneedle substrates obtained in step 7, and removing the material on regions reserved on both sides of the substrates 6 to separate the sheet in-plane metal microneedles from the metal sheets 5 to obtain a sheet in-plane microneedle array as shown in FIG. 5.

Figure 9:
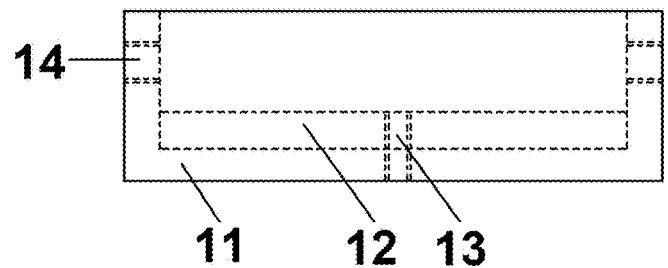
FIG. 9 is a front view in three views of an assembling and clamping device of a microneedle array.
Figure 10:
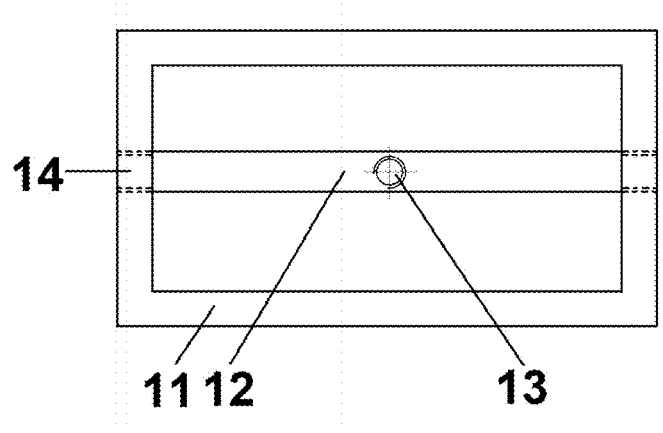
FIG. 10 is a top view in three views of an assembling and clamping device of a microneedle array.
Figure 11:
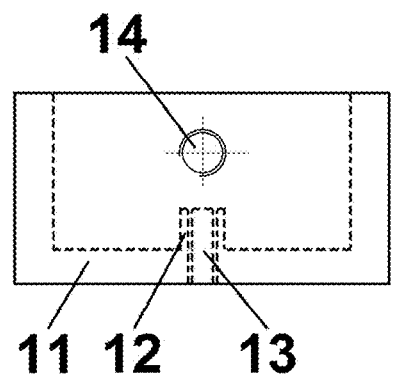
FIG. 11 is a side view in three views of an assembling and clamping device of a microneedle array.
Figure 12:
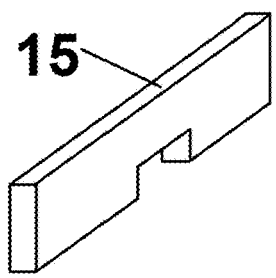
FIG. 12 shows a partition board for positioning a microneedle substrate in an assembling and clamping device of a microneedle array.

An assembling and clamping device of a high aspect ratio in-plane metal microneedle array is disclosed. A special microneedle sheet assembling and clamping device comprises a main body 11 and a partition board 15; and the main body 11 and the partition board 15 are made of aluminum alloy material. The whole clamping device is a box-shaped cuboid with one side open, and the bottom of an inner cavity is provided with a slide rail 12 matched with the groove at the bottom of each microneedle substrate of S9. As shown by the reference number "12" in FIGS. 9, 10 and 11, the sizes of the inner cavity are 25 mm in length, 20 mm in width, 10 mm in height and 5 mm in wall thickness. Threaded holes 13 for installing the hand-held handle are processed on the bottom of an assembling body, and threaded holes 14 are processed on the end surfaces of both sides of the assembling body for pressing the partition board 15 by bolts 16. Three views of the whole clamping device are shown in FIGS. 9, 10, and 11. In the present embodiment, the partition board 15 used for positioning is made of aluminum alloy material. The height of the partition board 15 is 10 mm, and the length of the partition board 15 needs to be consistent with the width of the cavity of the main body 11, i.e., 20 mm. The width of the partition board 15 is set as required, and is 3.5 mm in the present embodiment; and the number of the partition boards is 7. The bottom of each partition board 15 is provided with a groove consistent with the size of the groove at the bottom of each microneedle substrate.

Figure 13:
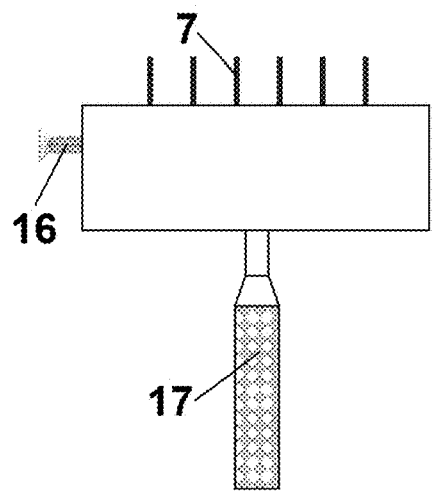
FIG. 13 is a front view in a schematic diagram after assembling and clamping of a microneedle array.
Figure 14:
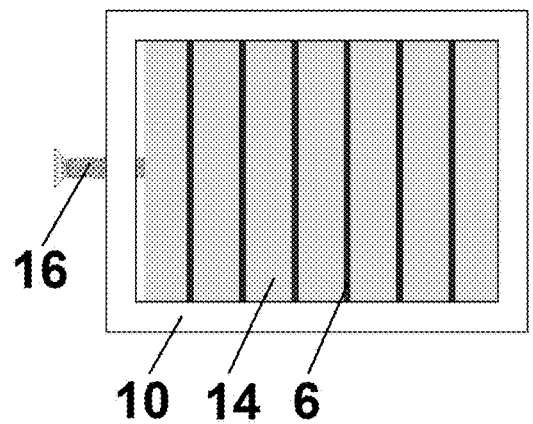
FIG. 14 is a top view in a schematic diagram after assembling and clamping of a microneedle array.
Figure 15:
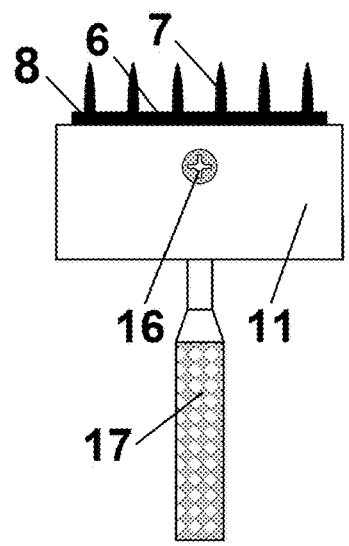
FIG. 15 is a side view in a schematic diagram after assembling and clampiece of a microneedle array.

The sheet in-plane microneedle array and the partition board 15 as shown in FIG. 5 are arranged in sequence and placed in the main body 11 of the clamping device. The threaded through holes 14 as shown in FIGS. 9, 10, and 11 on the end surface of any side of the bolt clamping device are used to compact and fix the microneedle substrates and the partition board. The hand-held handle 17 is installed in the threaded hole 13 at the bottom of the clamping device, and finally the organized microneedle array shown in FIGS. 13, 14 and 15 is obtained.

Figure 16:
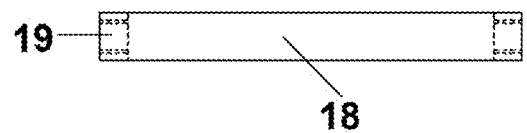
FIG. 16 is a front view in three views of an inserting auxiliary device of a microneedle array.
Figure 17:
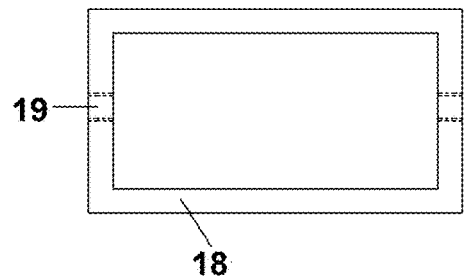
FIG. 17 is a front view in three views of an inserting auxiliary device of a microneedle array.
Figure 18:
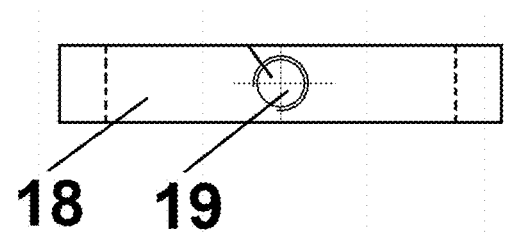
FIG. 18 is a front view in three views of an inserting auxiliary device of a microneedle array.

An inserting auxiliary device of a high aspect ratio in-plane metal microneedle array is disclosed. The inserting auxiliary device comprises a rectangular frame main body 18, a positioning partition board 20, and positioning small spacers 21, as shown in FIGS. 16, 17 and 18. The rectangular frame main body 18 and the positioning partition board 20 are made of aluminum alloy material. The positioning small spacers 21 and the microneedle substrates 6 are made of the same material.

The rectangular frame main body 18 is a frame-shaped cuboid which is open up and down, and is arranged above the assembling and clamping device. The length and the width of an inner frame are consistent with the length and the width of the cavity of the main body 11 of the clamping device. The height of the rectangular frame main body 18 needs to be matched with the sizes of the positioning shoulders 8 shown in FIG. 5. In the present embodiment, the sizes of the part are 3 mm in height and 3 mm in width. The height needs to be consistent with the size of the microneedle substrate above the partition board. Both sides of the rectangular frame main body 18 are provided with threaded through holes 19 through which capless bolts 22 pass, for subsequent tightening.

Figure 19:
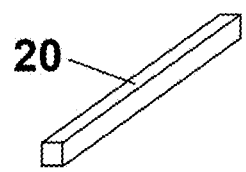
FIG. 19 shows a partition board for positioning a microneedle spacer in an inserting auxiliary device of a microneedle.
Figure 20:
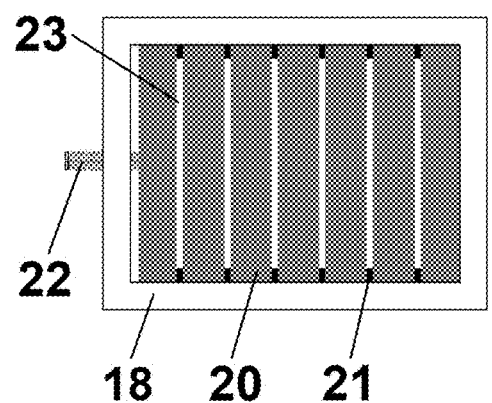
FIG. 20 is a schematic diagram after assembling of an inserting auxiliary device of a microneedle array.

The positioning partition board 20 is specifically shown in FIG. 19. The height of the positioning partition board 20 is consistent with the height of the rectangular frame main body 18, which is 3 mm. The length of the positioning partition board 20 is consistent with the length of the partition board 15 of the clamping device, which is 20 mm. The thickness of the positioning partition board 20 is consistent with the thickness of the partition board 15 of the clamping device, and the corresponding positions of the positioning partition board 20 and the microneedle bodies are lightly sanded with fine sandpaper. Every two positioning partition boards 20 are separated by the positioning small spacer 21, and a gap 23 between the two positioning partition boards 20 is used for the microneedle bodies 7 to pass. The height of the positioning small spacers 21 is consistent with the height of the positioning partition board 20, which is 3 mm. The width of the spacers should be slightly smaller than the width of the positioning shoulders 8 as shown in FIG. 5 in S9, and in the present embodiment, the width is 2.8 mm. The thickness is consistent with the thickness of the microneedle substrates. A positioning frame, the partition board and the spacers in S24 are assembled, and the inserting auxiliary device of the microneedle array as shown in FIG. 20 is finally obtained.

The positioning partition board 20 is assembled into the rectangular frame main body 18; the positioning small spacers 21 are placed at both ends of each positioning partition board 20 to make the distance of the positioning partition boards 20 consistent with the thickness of the microneedles. The capless bolts are used for compacting and encapsulating from one side of the rectangular frame main body 18 to compact the positioning partition board 20 and the positioning small spacers 21 to obtain the inserting auxiliary device of the microneedle array as shown in FIG. 20. 502 glue is used at both ends of the positioning partition boards 20 to reinforce the connection among the partition boards 20, the positioning small spacers 21 and the rectangular frame main body 18. The finally assembled inserting auxiliary device is shown in FIG. 20. A skin region to be applied with drugs is sterilized; the assembled inserting auxiliary device as shown in FIG. 20 is placed on the skin; and the assembled microneedle array as shown in FIGS. 13, 14 and 15 is inserted into the skin through the gap 23 of the positioning partition boards 20 in the auxiliary device.

The embodiments of the present invention are only used for describing and explaining the technical solution of the present invention rather than limitation. Although the present invention is described in detail with reference to the preferred embodiments, those ordinary skilled in the art shall understand that the technical solution of the present invention can be amended or equivalently replaced without departing from the spirit and the scope of the technical solution of the present invention. The amendment or equivalent replacement shall be covered within the scope of the claims of the present invention.

The invention claimed is:

1. A manufacturing method for an in-plane metal microneedle array, the method comprising the following steps:
   step 1: using medical stainless steel or titanium alloy metal sheet material as a microneedle material, wherein a thickness of the metal sheet is 20-200 microns;
   step 2: cutting the metal sheet into smaller metal sheets, wherein each smaller metal sheet has a length of 30-50 mm and a width of 10-30 mm;
   step 3: processing a special sheet clamping tooling;
   the tooling is composed of two identical upper and lower metal cover plates, and an overall thickness of each cover plate is 5-10 mm; inner walls of the upper and the lower cover plates of the tooling are processed with grooves, each groove has a length and a width matching the length and the width of the smaller metal sheet for receiving the smaller metal sheet therein;
   a depth of each groove of the upper and lower cover plates are 1-5 mm; through holes for passing through fastening bolts are processed at edges around the upper and lower cover plates;
   step 4: placing a number of the smaller metal sheets in one of the grooves of one of the upper and lower cover metal cover plates; adjusting the number of the smaller metal sheets placed at one time according to a combined thickness of the smaller metal sheets and the depth of the one of the grooves; placing the other one of the upper and lower metal cover plates on the one metal cover plate on which the smaller metal sheets are placed, with the one of the grooves facing the smaller metal sheets and aligned up and down; then encapsulating and fastening the upper and the lower metal cover plates by the fastening bolts, and compacting the smaller metal sheets to form a whole with the upper and the lower metal cover plates, wherein the number of the smaller metal sheets placed at one time is in a range of 20-200;
   step 5: designing geometries and sizes of sheet in-plane metal microneedles;
   a sheet in-plane metal microneedle array is composed of substrates and microneedle bodies for a subsequent clamping part; the microneedle bodies are arranged above the substrates; positioning shoulders are arranged on both sides above the substrates for positioning guidance of an inserting auxiliary device; a positioning guide groove is arranged in a lower middle of each substrate for subsequent assembly of each substrate;
   step 6: clamping the smaller metal sheets and the tooling encapsulated in step 4 to a wire cutting device, determining a wire path according to the geometries and sizes of the sheet plane metal microneedles designed in step 5 by the wire cutting device, conducting wire cutting on the tooling and the smaller metal sheets as a whole, and processing the smaller metal sheets into the substrates and the microneedle bodies; in the wire cutting process, the tips of the microneedle bodies are cut in a figure 8-shape to ensure sharpness of microneedle tips; during processing, both sides of the substrates are reserved for 2 to 5 mm without cutting to ensure that the clamping tooling and the smaller metal sheets still form a whole after processing;
   step 7: taking off the fastening bolts on the tooling, and taking out and washing the processed smaller metal sheets to obtain microneedle substrates which are not cut;
   step 8: cutting the microneedle substrates obtained in step 7, and removing the material on regions reserved on both sides of the substrates to separate the sheet in-plane metal microneedles from the smaller metal sheets to obtain a sheet in-plane metal microneedle array with a plurality of microneedle bodies;
   wherein a height of each microneedle body is 1-5 mm, a width of a root of each microneedle body is 50-500 microns, and a thickness of each microneedle body is the thickness of the metal sheet; the number of the microneedles on each substrate is 3-50, and a distance between each pair of microneedles is 0.25-10 mm; positioning shoulders are arranged on both sides above the substrates for positioning guidance of an inserting auxiliary device; a positioning guide groove is arranged in the lower middle of each substrate for subsequent assembly of each substrate;
   the microneedle bodies adopt equal-strength design along a length direction, that is, the width change of the microneedle bodies needs to ensure that the microneedle bodies have same maximum bending stress at each cross section when tips are subjected to a transverse concentrated load; if the root of each microneedle body is a starting point of x axis, the x axis is located on a longitudinal symmetry axis of each microneedle body, and a width direction is assumed to be a y axis, then the equal-strength design requires that x and y satisfy the following relationship in the following formula:

$$y = \pm C\sqrt{L_0 - x};$$

wherein $L_0$ is the length of the microneedle bodies, and C is a constant which comprehensively reflects the yield strength of the material, the thickness of the microneedles, and a load size.

2. The manufacturing method for the in-plane metal microneedle array according to claim 1, wherein the clamping tooling is made of metal material selected from a group including stainless steel and 45 #steel.

* * * * *